(12) United States Patent
Mann et al.

(10) Patent No.: US 9,901,108 B2
(45) Date of Patent: Feb. 27, 2018

(54) MYCOTOXIN-REDUCING COMPOSITION

(71) Applicants: Stephen Philip Mann, Cambridge (GB); David Parfitt, Bridgewater (GB)

(72) Inventors: Stephen Philip Mann, Cambridge (GB); David Parfitt, Bridgewater (GB)

( * ) Notice: Subject to any disclaimer, the term of this patent is extended or adjusted under 35 U.S.C. 154(b) by 121 days.

(21) Appl. No.: 14/577,567

(22) Filed: Dec. 19, 2014

(65) Prior Publication Data

US 2015/0150285 A1 Jun. 4, 2015

Related U.S. Application Data (62) Division of application No. 12/447,837, filed as application No. PCT/GB2007/004191 on Nov. 1, 2007, now abandoned.

(30) Foreign Application Priority Data

Nov. 1, 2006 (GB) .................................. 0621792.1

(51) Int. Cl.

| | | |
|---|---|---|
| *A01N 63/04* | (2006.01) | |
| *A23L 1/015* | (2006.01) | |
| *A61K 31/715* | (2006.01) | |
| *A61K 33/06* | (2006.01) | |
| *A61K 36/064* | (2006.01) | |
| *A61K 38/44* | (2006.01) | |
| *A61K 38/46* | (2006.01) | |
| *A61K 38/47* | (2006.01) | |
| *A61K 38/48* | (2006.01) | |
| *A23K 10/10* | (2016.01) | |
| *A23K 10/18* | (2016.01) | |
| *A23K 10/38* | (2016.01) | |
| *A23K 20/163* | (2016.01) | |
| *A23K 20/189* | (2016.01) | |
| *A23K 10/14* | (2016.01) | |
| *A23K 20/28* | (2016.01) | |
| *A23K 50/10* | (2016.01) | |
| *A23L 5/20* | (2016.01) | |

(52) U.S. Cl.
CPC ............ *A23L 1/0153* (2013.01); *A23K 10/10* (2016.05); *A23K 10/14* (2016.05); *A23K 10/18* (2016.05); *A23K 10/38* (2016.05); *A23K 20/163* (2016.05); *A23K 20/189* (2016.05); *A23K 20/28* (2016.05); *A23K 50/10* (2016.05); *A23L 5/25* (2016.08); *A23L 5/27* (2016.08); *A23L 5/273* (2016.08); *A23L 5/28* (2016.08); *A61K 31/715* (2013.01); *A61K 33/06* (2013.01); *A61K 36/064* (2013.01); *A61K 38/44* (2013.01); *A61K 38/443* (2013.01); *A61K 38/46* (2013.01); *A61K 38/465* (2013.01); *A61K 38/47* (2013.01); *A61K 38/48* (2013.01); *C12Y 101/00* (2013.01); *C12Y 104/03* (2013.01); *C12Y 104/03002* (2013.01); *C12Y 104/03003* (2013.01); *C12Y 111/01007* (2013.01); *C12Y 111/01013* (2013.01); *C12Y 301/01* (2013.01); *C12Y 301/01003* (2013.01); *C12Y 301/01025* (2013.01); *C12Y 302/01* (2013.01); *C12Y 303/02003* (2013.01); *C12Y 304/00* (2013.01); *A23V 2002/00* (2013.01); *C12Y 302/01004* (2013.01); *Y02P 60/873* (2015.11)

(58) Field of Classification Search
CPC .... A23L 1/0153; A23L 1/0155; A23L 1/0156; A23L 1/0158; A23L 5/25; A23L 5/27; A23L 5/273; A23L 5/28; C12Y 101/00; C12Y 104/3002; C12Y 104/3003; C12Y 111/1007; C12Y 111/1013; C12Y 201/1003; C12Y 301/1025; C12Y 303/2003; C12Y 304/001; C12Y 104/03; C12Y 301/01; C12Y 302/011; C12Y 302/1004; A61K 33/06; A61K 36/064; A61K 38/44; A61K 38/443; A61K 38/46; A61K 38/465; A61K 38/47; A61K 38/48; A23K 10/10; A23K 10/14; A23K 10/18; A23K 10/38; A23K 1/006; A23K 1/009; A23K 1/06; A23K 1/1643; A23K 1/1653; A23K 1/1656; A23K 1/1756; A23K 1/1813; A23K 20/163; A23K 20/189; A23K 20/28; A23K 50/10; Y02P 60/873
See application file for complete search history.

(56) References Cited

U.S. PATENT DOCUMENTS

| | | | |
|---|---|---|---|
| 4,305,876 A | 12/1981 | Barner et al. | |
| 5,165,946 A * | 11/1992 | Taylor ................... | A23K 20/28 426/271 |
| 5,716,820 A | 2/1998 | Duvick et al. | |
| 2004/0208956 A1 | 10/2004 | Schatzmayr et al. | |
| 2005/0079352 A1 | 4/2005 | Glorioso et al. | |
| 2006/0045934 A1 | 3/2006 | Kabse et al. | |

(Continued)

FOREIGN PATENT DOCUMENTS

| | | |
|---|---|---|
| WO | WO 96/12414 | 5/1996 |
| WO | WO 96/12414 A1 * | 5/1996 |

(Continued)

OTHER PUBLICATIONS

Avantaggiato et al. Food Chem. Toxicol. (2004) 817-824.*
Garda et al. Food Control (Jun. 2005) 16: 423-428.*
Poppenberger et al. J. Biol. Chem. (2003) 278(48): 47905-47914.*
English translation of WO 96/12414 downloaded from the EPO May 26, 2017.*
English translation of WO 2006/053357, May 26, 2006, Schatzmayr et al.
English translation of WO 96/12414, May 2, 1996, Erber.
Trenholm, H.L. et al. "Mycotoxin Binding Agents: an Update on What We Know" *Zootecnia International*, Sestri Levante, IT, 1997, 20(1): 40-42.
Erber Aktiengesellschft. "Mycofix® Plus . . . always a step ahead in mycotoxine deactivation" 2004, 2 pages.
Verma, D.S. "Mycotoxin Biotransformation: Latest approach to well known problem in Indian feed industry" *Poultry Line*, Aug. 2005, 2 pages.

(Continued)

*Primary Examiner* — Susan M Hanley
(74) *Attorney, Agent, or Firm* — Saliwanchik, Lloyd & Eisenschenk (57) ABSTRACT

A composition comprising an enzyme, a mycotoxin-binding agent and a microorganism capable of taking up a mycotoxin.

12 Claims, 6 Drawing Sheets

(56) References Cited

U.S. PATENT DOCUMENTS

| | | | |
|---|---|---|---|
| 2006/0188549 A1 | 8/2006 | Block et al. | |
| 2006/0240567 A1* | 10/2006 | Brown | C07K 14/001 436/514 |
| 2007/0065413 A1 | 3/2007 | Castillo | |
| 2007/0166446 A1 | 7/2007 | Boursier | |

FOREIGN PATENT DOCUMENTS

| | | |
|---|---|---|
| WO | WO 99/53772 | 10/1999 |
| WO | WO 00/65928 | 11/2000 |
| WO | WO 2005/079584 | 9/2005 |
| WO | WO 2006/053357 | 5/2006 |

OTHER PUBLICATIONS

Verma, D.S. "Combined Strategies Guarantee Mycotoxin Control" *Asian Nutrition Forum*, 2007, 3 pages.
Devegovda, G. et al. "Mycotoxin Picture Worldwide: Novel Solutions for Their Counteraction" *Biotechnology in the Feed Industry*, Alltech's Fourteenth Annual Symposium, Nottingham University Press. Nottingham, United Kingdom, 1998, pp. 241-255.
Shapira, R. et al. "Control of mycotoxins in storage and techniques for their decontamination" *Mycotoxins in Food*, Woodhead Publishing Limited, Cambridge, England, 2004, pp. 190-223.
Jouany, J.P "Methods for preventing, decontaminating and minimizing the toxicity of mycotoxins in feeds" *Animal Feed Science and Technology*, 2007, 137:342-362.
Pettersson, H. "Controlling mycotoxins in animal feed" Woodhead Publishing Limited, 2004, 43 pages.
TOXY-NIL™ Plus, Nutri-Ad International BVBA, Kasterlee, Belgium, 1999, 4 pages.
Etikett "Biomix" Sep. 6, 2010, 1 page (original Spanish version).
Etikett "Biomix" Sep. 6, 2010, 1 page (German translation of R11).
Etikett "Biomix" Sep. 6, 2010, 2 pages (English translation of R12).
Zhang, K. et al. "Screening multimycotoxins in food-grade gums by stable isotope dilution and liquid chromatography/tandem mass spectrometry" *J. AOAC Int'l.*, 2014, 97(3):889-895.
Nurminen, T. et al. "The lipolytic activities of the isolated cell envelope fractions of baker's yeast" *Biochem. J.*, 1970, 118:759-763.
Definition of "express" from http://en.mimi.hu.org/biology/express.htm, 5 pgs.
Shetty, P.H. et al. "*Saccharomyces cerevisiae* and lactic acid bacteria as potential mycotoxin decontaminating agents" *Trends Food Sci. Tech.*, 2006, 17:48-55.
Avantaggiato, G. et al. "Recent advances on the use of adsorbent materials for detoxification of *Fusarium* mycotoxins" *Food Additives & Contaminants*, 2005, 22(4):379-388.
Ishii, K. "Trichothecenes—Chemical, Biological and Toxicological Aspects" in *Developments in Food Science 4*, Ueno, Y., Ed., 1983, pp. 7-19.

\* cited by examiner

MYCOTOXIN-REDUCING COMPOSITION

CROSS-REFERENCE TO RELATED APPLICATIONS

The present application is a divisional of U.S. application Ser. No. 12/447,837, filed Sep. 15, 2009, which is the National Stage of International Application Number PCT/GB2007/004191, filed Nov. 1, 2007, each of which is hereby incorporated by reference herein in its entirety, including any figures, tables, nucleic acid sequences, amino acid sequences, or drawings.

FIELD OF THE INVENTION

This invention relates to reducing the mycotoxin content of a foodstuff.

BACKGROUND OF THE INVENTION

Mycotoxins are toxins produced by funghi that are known to affect adversely the nutrition and health of humans and animals. The production of mycotoxins is the result of the natural biological process of funghi and has occurred over thousands of years. However, mycotoxin production has been influenced by climate change and changes in agricultural practise.

Mycotoxins are produced by a wide range of funghi including *Aspergillus* (Aflatoxin and Ochratoxin), *Fusarium*, (Zearalenone, Deoxynivalenol, Fumonisin) and *Penicillium* (PR toxin and Roquefortin). These toxins have a considerable pharmacological effect, even at very low concentrations (parts per billion), while toxicity may be further enhanced by metabolism in vivo, particularly by the liver. Detoxification of most toxins occurs in the liver, while in the gastro-intestinal tract (GIT), under certain conditions, detoxification may also be achieved by micro-organisms.

A large number of mycotoxins have been identified. Currently, there are five main groups of particular agricultural interest: the Aflatoxins, the trichothecene (for example Deoxynivalenol), the Zearalenone group, the Fumonisins and the endophyte toxins.

Aflatoxins can cause growth reduction, suppressed immunity, reduced feed efficiency and increased mortality in cattle, among other symptoms. In pigs, reduced feed efficiency, increased mortality, and lower growth rates can be observed. In poultry, there are similar symptoms and a decreased ability to metabolize fat, protein and starch.

Zearalenone in cattle and pigs mimics oestrogen and produces a considerable reduction in reproductive performance, reduced growth, reduced milk production and reduced feed efficiency. In poultry, increased mortality is observed.

Deoxynivalenol (DON), an example of a trichothecene, causes severe symptoms in cattle, pigs and poultry, including gastric effects such as vomiting, reduced growth rates, reduced egg production, scours and reduced feed efficiency.

Fumonisin produces negative effects via a reduction in blood circulation and cardiac output, at least in part by agonising sphingosine receptors. In this way they reduce growth and cause pulmonary oedema in swine and poultry. This reduction of circulation affects all major organs including the liver and can exacerbate and enhance the effects of other toxins that may also be present.

Ochratoxin can be carcinogenic in man and produces immuno-supression in farm animals.

Lolitrem B (*Acremonium* lolii in Ryegrass) is an example of an endophyte toxin that produces a form of grass staggers often confused with hypomagnesaemia.

Sporidesmin (*Pithomyces* spp. in Ryegrass) is an endophyte that causes facial eczema and liver damage in sheep.

Ergovaline (*Acremonium coenophialum*) is an endophyte toxin found in tall fescue, which reduces prolactin release and reduces blood flow.

It is in the interests of the health of both humans and animals that mycotoxins are reduced, or preferably removed altogether, from the food chain.

Current techniques used to reduce mycotoxin content in a foodstuff involve the use of mycotoxin-binding agents, such as bentonite clay, to which the toxins bind and can therefore be removed with the clay. However, binding and removal of mycotoxins are only partly successful. Some mycotoxins remain toxic even when attached to a binding agent, while some toxins do not bind efficiently at normal in vivo concentrations. Higher contamination levels are also an issue as the current recommended levels of binders may not be sufficient to remove all toxins present.

An alternative technique is to add to foodstuffs enzymes, or microorganisms, that break down mycotoxins, to reduce toxicity. However, this is often not effective at reducing mycotoxin content sufficiently, which may be due to a dynamic equilibrium in the gasto-intestinal tract, which prevents excretion of the toxins.

An effective technique for reducing mycotoxin toxicity is therefore still required.

SUMMARY OF THE INVENTION

The present invention is based on the surprising realisation that a composition containing an enzyme, a mycotoxin-binding agent and a microorganism capable of taking up a mycotoxin is unexpectedly effective at reducing mycotoxin toxicity.

According to a first aspect of the invention, a composition comprises an enzyme, a mycotoxin-binding agent and a microorganism capable of taking up a mycotoxin.

According to a second aspect of the invention, a method of reducing the toxicity of a mycotoxin in a foodstuff comprises the step of contacting the foodstuff with a composition as defined above.

According to a third aspect of the invention, a foodstuff comprises a composition as defined above.

According to a fourth aspect of the invention, a composition as defined above is useful in therapy, in particular the treatment of a disease caused by a mycotoxin.

According to a fifth aspect of the invention, a composition as defined above is used in the manufacture of a medicament for the treatment of a disease caused by a mycotoxin.

BRIEF DESCRIPTION OF THE FIGURES

The invention is described with reference to the following figures, wherein.

DETAILED DESCRIPTION OF THE INVENTION

The invention is based on the finding that combining an enzyme, a mycotoxin-binding agent and a microorganism that is capable of taking up a mycotoxin is surprisingly effective at reducing the toxicity of mycotoxins present in a foodstuff.

The present inventor has realised that, when an enzyme alone is used, a dynamic equilibrium exists that prevents toxins from being defecated. Therefore, the sequestration by a microorganism and binding by a binding agent act as an aid to the ultimate degradation of the toxin by the enzymes and, optionally, microorganisms in the composition.

As used herein, the term "enzyme" is to be given its usual meaning in the art, i.e. a biological catalyst. For the avoidance of doubt, an enzyme is a protein. The enzyme is preferably at least partially purified, i.e. is provided as a cell extract, isolate or purified preparation. The enzyme is present in the composition in addition to any enzymes present in the microorganism, i.e. the enzymes, microorganism and mycotoxin-binding agent are present as three separate components of the composition. The purpose of the enzyme in the composition of the invention is to modify one or more mycotoxins, to reduce the toxicity of the toxin. Preferably, the enzyme breaks down the toxin, partially or completely, thereby removing the toxicity of the toxin.

Therefore, the one or more enzymes of the composition preferably break down the toxin. The enzyme may further induce a modification of a toxin so that binding to the binding agent is increased, pending further degradation. Without wishing to be bound by theory, the inventor believes that epoxidation and/or dehydrogenation of the toxin, in particular, improves binding. An increase in binding of the toxin to the binding agent may be detected by a toxin binding assay, as detailed in Example B, experiment 4 . Other enzymes, that do not necessarily act directly upon a mycotoxin, may be used to produce radicals that modify the toxin.

This may be achieved with or without binding of the toxin to the enzyme. An example of a suitable enzyme of this type is lignin peroxidase. In this embodiment, where radicals are used, the enzyme may be replaced with a biomimetic catalyst (such as the haem prosthetic group), an organometallic catalyst or a metallic catalyst.

Any enzyme, or combination of enzymes, with the ability to reduce the toxicity of a mycotoxin is within the scope of the invention. Preferred enzymes include an esterase, lipase, protease, oxidase, amino acid oxidase, lactonohydrolase, peroxidase, lactoperoxidase, manganese peroxidase, epoxidase, polysaccharase and dehydrogenase. Any combination of preferred enzymes can be used and the skilled person will realise that the specific combination of enzymes required may depend on the toxin or toxins to be treated. Particularly preferred enzymes include cellulases, epoxidases, dehydrogenases, hemicellulases (also known as xylanases) and lipases, preferably a triacylglycerol lipase (E.C. number 3.1.1.3), such as lipase AE 02 (obtainable from *Candida* Rugosa and commercially available from Mann Associates, Cambridge, UK) or "Lipase OF" (commercially available from Meito Sangyo, Japan). The combination preferably includes a lipase. A preferred combination of enzymes is the combination of a cellulase, a hemicellulase (xylanase) and a lipase. A preferred combination of enzymes suitable for use in the invention is shown in Table 2, below.

The second component of the composition according to the invention is a mycotoxin-binding agent. One or more binding agents can be included. Preferably, 2, 3, 4 or more different binding agents are included. The term "binding" refers both to ionic or covalent chemical bonding and weaker physical adsorption involving van der waals interactions and/or hydrogen bonding. In a preferred embodiment, the binding agent has a charged surface. The charge may be positive or negative. Binding refers to the non-transient association of a mycotoxin to the binding agent. In a preferred embodiment, the binding has a minimum affinity between the mycotoxin and binding agent such that 10 mg of binding agent will bind 50% of a 200 μg/l (i.e. physiological) concentration of toxin. Binding may be determined using the method provided in Example B, experiment 4 . Mycotoxin-binding agents are known in the art; examples of suitable binding agents are zeolites, montmorillonite, bentonite clays, diatomaceous earth, activated charcoals, fibrous plant materials such as wheat bran and alfalfa fibre, yeast cell wall extract and polysaccharides. Any agent that can bind a mycotoxin or a mycotoxin breakdown product is within the scope of the invention. Preferred mycotoxin-binding agents include a bentonite clay, preferably sodium bentonite or more preferably calcium bentonite, and a polysaccharide, preferably glucomannan, more preferably an esterified glucomannan. The glucomannan is preferably obtained as a yeast cell wall extract, as is recognised in the art. Glucomannan-containing mycotoxin adsorbents are commercially available, for example Mycosorb®, obtainable from Alltech UK, Stamford, UK.

Preferably, the binding agent has at least one ionic, i.e. charged, surface, which will allow (strong) ionic bonding between the toxin and binding agent to occur. The charge may be positive or negative. Examples of ionic binding agents are bentonites such as sodium bentonite and calcium bentonite.

The third component of the composition according to the invention is a microorganism. As used herein, the term "microorganism" refers to bacteria and yeasts. The skilled person will recognise that the microorganism is preferably not harmful to the health of the human or animal which will ingest the foodstuff to which the composition will be applied, i.e. the microorganism is preferably non-pathogenic. The purpose of the microorganism is to uptake mycotoxins. Any microorganism that can uptake mycotoxins can be used according to the invention. Once taken up, the microorganism sequesters the toxin, which cannot then be taken up by the host animal. The microorganism's endogenous enzymes may then breakdown the toxins, although this is not an absolute requirement. Preferably, the microorganism is a yeast, more preferably a saccharomyces, most preferably *Saccharomyces cerevisiae.*

The microorganism has the function of physically taking up the toxin to sequester it within the bacterial or yeast cell. In the case of one toxin at least (DON), the toxin is modified in the cell and analogues are released, which are then able to bind to the binders where further enzyme degradation can take place. Therefore, in a preferred embodiment, the microorganism additionally performs a second function, that of expressing one or more enzymes capable of breaking down a mycotoxin.

One or more different microorganisms can be included in the composition of the invention. In one embodiment, at least two microorganisms are included; the first microorganism is primarily responsible for mycotoxin uptake and the second is primarily responsible for mycotoxin degrading enzyme expression. For the avoidance of doubt, in the embodiments where a microorganism expresses one or more enzymes capable of breaking down a mycotoxin, the composition must still contain the enzyme component as a separate component of the composition.

subsequently combined with the additional components when needed for application to a foodstuff.

Any amount of each of the three essential components of the composition can be used that achieves the desired result of reducing mycotoxin levels. Preferably, between 0.1 kg and 50 kg of the composition is applied to each tonne of feed, more preferably between 0.2 kg and 10 kg per tonne, e.g. 0.5, 1, 1.2, 1.5, 2.5, 5, 7.5 kg or more per tonne. Suitable levels will be apparent to the skilled person.

TABLE 1

Example Composition according to the Invention.

| Name | Source/Company | Specification | kg | Approx % wt |
|---|---|---|---|---|
| FerMos Mannan oligosaccharide (Binding Agent) | JACKLYN IND | FerMos, 25 kg Bags | 7.445 | 35% |
| Terra-Green 24/48 LVM (Binding Agent) | OIL DRI | Terra-Green, 24/48 LVM, 50 lb bags | 6.68742 | 30% |
| Sodium bentonite (Binding Agent) | Eastern Mineral | Sodium Bentonite Granular | 2.06116 | 10% |
| Diabond Granular (Binding Agent) | Eastern Mineral | 200 Bags of Diabond granular, 50 lb bags | 2.06116 | 10% |
| Dried molasses | Bartlett Milling | Dried molasses, 50 lb bags. | 1.03058 | 5% |
| S. cerevisiae Yeast | JACKLYN IND | Bulk Yeast 10 B/g, 20 kg box | 1 | 5% |
| Vitamin A, A-30 | RC BWATER | Vitamin A, A-30, 50 lb bag | 0.51529 | 2% |
| Vitamin E, E-20 | RC BWATER | Vitamin E, E-20, 50 lb bag | 0.51529 | 2% |
| Enzyme Premix IV (See Table 2) | Micron | Mycotex SW enzymes | 0.03405 | <1% (0.16%) |
| Light mineral oil | AKEY | Light mineral oil, 387 lb drum | 0.22809 | 1% |
| TOTAL | | | 21.53204 | 100.00% |

TABLE 2

Enzyme Formulation suitable for use in the Composition of the Invention

| Name | Source | Specification | kg | % wt |
|---|---|---|---|---|
| Cellulase 300 TR | BIOCAT | Cellulase 300 TR, 75,000/g, | 0.49000 | 32.67% |
| Hemicellulase 1500 | BIOCAT | Hemicellulase 1500 | 0.49000 | 32.67% |
| Lipase OF | Meito Sangyo | 400,000 U/g | 0.49000 | 32.67% |
| Flow Agent | DUNLEARY | Hubersorb 600, 30 lb bag | 0.03000 | 2.00% |
| TOTAL | | | 1.50000 | 100.00% |

In addition to these essential components, additional components can be included in a composition of the invention, if necessary. Examples of suitable additional components are food supplements such as vitamins and minerals, mineral oil, a flow agent such as a fine, precipitated calcium silicate powder (e.g. hubersorb), and a sugar source such as dried molasses. An example of a formulation according to the invention is provided in Table 1.

The three essential components are preferably prepared as a mixture, optionally with a flow agent (as in Table 2), and In a preferred embodiment, the composition is applied to the feed such that the microorganism is present at approximately $1\times10^9$ cells per tonne of feed or greater. More preferably, the microorganism is present at $2\times10^9$, $3\times10^9$, $4\times10^9$ or $5\times10^9$ cells per tonne of feed or greater. Yet more preferably, $1\times10^{10}$ cells per tonne of feed is applied, more preferably $1\times10^{11}$ cells per tonne of feed or greater is applied, for example greater than $2\times10^{11}$ cells per tonne of feed, more preferably greater than $1\times10^{12}$, $2\times10^{12}$ cells per tonne of feed or more. The skilled person will realise that the precise amount of composition that is required per tonne of feed will depend on the feed to be treated, the toxins present and the intended recipient of the feed. For example, an animal that consumes a small amount of feed per day will generally require a higher concentration of microorganism applied to the feed than an animal that consumes a large amount of feed per day. For cattle, an example of a suitable amount is $2.2\times10^{11}$ cells per tonne of feed, while for swine and poultry a preferred amount is $1.1\times10^{12}$ cells per tonne of feed.

In the composition, the microorganism is present at any suitable level that allows detoxification to occur when applied to a foodstuff. Preferably, the microorganism is present at approximately $1\times10^9$ cells or greater per kilogram of the composition, more preferably $1\times10^{10}$ cells per kilogram of composition, or greater, for example $1 \times 10^{11}$ or $1 \times 10^{12}$ cells per kilogram, or greater. The skilled person will appreciate that the amount of microorganism in the composition will affect the amount of composition required to achieve the desired effect, in particular the cells per tonne of feed recited above. In the example composition of Table 1, yeast is included at approx 5% (by weight). 1 Kg of the composition defined by Table 1 contains approximately $5 \times 10^{11}$ yeast cells. Therefore, applying 0.5 Kg of this composition to a tonne of feed will provide approximately $2.5 \times 10^{11}$ cells per tonne of feed, while applying 2.5 Kg of this composition to a tonne of feed will provide approximately $1.25 \times 10^{12}$ cells per tonne of feed.

The one or more enzyme is present in the composition at an effective level. Less than 5% by weight of enzyme is preferred, more preferably less than 1%, more preferably between 0.01% and 0.5% by weight, yet more preferably between 0.15% and 0.25% by weight. The composition of Table 1 contains an enzyme mixture totalling 0.16% by weight, including the flow agent.

The binder is present in the largest proportion, at an effective level. Preferably, at least 50% by weight of the composition should be binding agent, more preferably 60 to 90%. The composition of Table 1 contains a mixture of binding agents totalling approx 85%.

For the avoidance of doubt, a suitable range for each of the essential ingredients in the composition of the invention is: microorganism—0.1% to 10% by weight, preferably 2% to 8%, i.e. 5%; enzyme—less than 5% by weight of enzyme is preferred, more preferably less than 1%, more preferably between 0.01% and 0.5% by weight, yet more preferably between 0.15% and 0.25% by weight; binder—preferably at least 50% by weight of the composition is binding agent, more preferably 60 to 90%. The balance (if any) can be made up with the additional agents recited above, if required.

The composition of the invention can be in any suitable formulation, for example a solid such as a powder or granulate, a gel or a liquid. Preferably, the formulation is a solid, more preferably a powder.

The composition of the invention is effective at reducing mycotoxin levels. Preferably, the composition is used to reduce mycotoxins in a foodstuff. As used herein, the term "foodstuff" is to be given its usual meaning in the art, referring to any material that is eaten by a human or animal for nutrition. Foodstuffs comprise carbohydrates, fats and/or proteins among other components. The foodstuff can be of animal or vegetable origin. Human food and animal feeds are within the scope of the term. In a preferred embodiment, the foodstuff is an animal feed of plant origin, commonly known as fodder, more preferably a cereal foodstuff. The term "foodstuff" includes materials that must be processed before safe consumption by a human or animal. A preferred example of such a material are "distiller's grains". These grains, also known as "distiller's dried grains", are a cereal by-product of the distillation process. Distiller's grains are known in the art. Briefly, they are produced in distilleries by drying mash and are used commonly as a fodder for livestock, especially ruminants. Detoxifying distiller's grains, by reduction of mycotoxin content, is therefore within the scope of the invention.

The composition can be added to the foodstuff any way that is effective at reducing the mycotoxin content. Contact between the composition and foodstuff is required. The preferred method is to treat the foodstuff before ingestion to remove, preferably completely, the toxicity. This is "detoxification" of the foodstuff before consumption. An alternative method is to treat the feed immediately before ingestion, or simultaneous with ingestion, and to rely on the invention to complete the detoxification during digestion. This post-ingestion detoxification is particularly suitable for use in animals, preferably ruminants such as cattle and sheep.

A method of reducing the toxicity of a mycotoxin or mycotoxins in a foodstuff comprises the step of contacting the foodstuff with a composition as defined herein. The mycotoxin can be any mycotoxin. Preferred mycotoxins include Zearalenone, a trichothecene such as Deoxynivalenol, Aflatoxin, Fumonisin, Roquefortin, ochratoxin or an endophyte toxin, such as sporidesmin, ergovaline or Lolitrem B.

A foodstuff of any human or non-human animal, preferably non-human mammal, can be detoxified according to the invention. Preferably, the foodstuff is for a farm animal such as cattle, horses, pigs or poultry.

Without wishing to be bound by theory, detoxification is thought to be achieved in a number of ways, acting in synergy. The enzyme component breaks down toxins and/or improves the toxin binding to the mycotoxin-binding agent. The binding agent prevents the mycotoxins from being absorbed by the animal and allows their excretion. The microorganism uptakes and sequesters the toxins and may also break down the toxins. Any toxin that is released by the microorganism is thought to bind more strongly to the binding agent, where further degradation (by the enzymes) may occur. Therefore, the actions of the microorganism and/or enzyme are thought to potentiate the binding of the toxin to the binding agent. These three components therefore work in an advantageous complex synergy that could not be predicted.

The toxin may therefore be removed from the foodstuff by enzyme breakdown, by binding to the binding agent and/or sequestration in the micro-organism, thus removing it from the foodstuff; if detoxification occurs in an animal, the removal is ultimately from the gastrointestinal tract in faecal material. These sequestrations have the further effects of preventing absorption into the animal and facilitating the action of the enzymes of the invention in the gastrointestinal tract.

The skilled person will realise that the health of animals and humans can be adversely affected by the presence of a mycotoxin in a foodstuff. The compositions of the invention can therefore be used in therapy, to treat a disease caused by a mycotoxin.

The invention is further described with reference to the following non-limiting examples.

EXAMPLES

Example A - Experimental Degradation of Toxins and Identification of Catalysts

The modification of various toxins by enzymes was examined by screening the activity of a number of a selection of enzymes against various toxins. The change in the toxin was measured by a monoclonal antibody in an Elisa test. Since the monoclonal antibody retains, in many cases, the ability to cross react with the fragments produced by the enzyme catalysis, this provides a definitive screening tool but not a quantitative measure of the enzymes activity.

Suitable enzymes which may be used as part of the invention are shown in Table 3 and examples of their action are shown in Tables 4-6.

TABLE 3

Examples of the Enzymes suitable for use in the Composition of the Invention.

| ENZYME | EC NUMBER | ACTION |
| --- | --- | --- |
| Esterase | 3.1.1.x | Ester hydrolysis |
| Lipase | 3.1.1.3 | Ester hydrolysis |
| Protease | 3.4.x.x | Hydrolysis of peptides |
| Oxidase | 1.4.3 | Oxidations |
| Aminoacid oxidase | 1.4.3.2 & 3 | Oxidation of amino acid $NH_2$ |
| Lacotonohydrolase | 3.1.1.25 | Hydrolysis of lactones |
| Peroxidase | 1.11.1.7 | Peroxidation reactions |
| Lactoperoxidase | 1.11.1.7 | Peroxidation reactions |
| Manganese peroxidase | 1.11.1.13 | Production of $Mn^{+++}$ |
| Epoxidase | 3.3.2.3 | Hydrolysis of peroxides |
| Polysaccharase | 3.2.1 | Hydrolysis of sugar cross links |
| Dehydrogenases | 1.1 | Oxidation by removal of hydrogen |

Experiment 1: Fumonisin Modification by Lipase

Lipase AE 02 (Mann Associates, Cambridge, UK) was incubated with Fumonisin 200 μg/liter and measured after 1 hour at 37° C. The remaining fumonisin was measured by ELISA assay. Boiled enzyme controls were also used in each case. It can be seen that there was a considerable reduction in the Fumonisin reacting with the antibody indicating degradation of the toxin.

TABLE 4

|  | pH 6.4 | pH 4.5 | No Buffer |
| --- | --- | --- | --- |
| Std Norm | 0.06 | 0.045 | 0.028 |
| Experimental | 0.039 | 0.046 | 0.01 |
| % degradation | 30 | 0 | 50 |
| Std boiled | 0.049 | 0.054 | 0.046 |
| Experimental | 0.039 | 0.046 | 0.014 |
| % degradation | 22 | 15 | 70 |

Experiment 2: Fumonisin Modification by Lipase and Amine Oxidase

Fumonisin was further examined by incubating it as in Table 3, but with an aminoxidase to remove the amine groups. The lipase 2 again achieved degradation while the oxidase also degraded the toxin. There was no apparent synergy of using both enzymes. This demonstrates that a combination of enzymes, alone, is not effective at improving mycotoxin degradation.

TABLE 5

|  | Blank | Lipase AEO 2 | Oxidase | Lipase AE 02 + Oxidase |
| --- | --- | --- | --- | --- |
| Results | 0.38 | 0.45 | 0.41 | 0.46 |
| % max abs Ave | 20.89 | 24.91 | 22.6 | 23.23 |
| ppm | 0.26 | 0.18 | 0.2 | 0.19 |
| % degradation |  | 31.90% | 22.10% | 26.00% |

Experiment 3: Enzyme modification of Zearalenone

Enzyme degradation of Zearalenone was examined using a variety of preparations. Of these preparations, some achieved degradation but the composition according to the invention (as defined in Table 1) produced a synergistic effect. Repeats of the experiment followed by analysis by HPLC showed that the formulation was capable of reducing the toxin levels to zero.

TABLE 6

| Enzyme | Formulation defined in Table 1 | Cellulase From Table 2 | Xylanase of Table 2 | Nitrilase (Control) | Lipase AE 02 |
| --- | --- | --- | --- | --- | --- |
| Experimental | 0.0010 | 0.014 | 0.022 | 0.024 | 0.006 |
| Control | 0.019 | 0.015 | 0.026 | 0.017 | 0.012 |
| % reduction in apparent toxin concentration | 47 | 7 | 17 | 0 | 12 |

Example B - Experimental Binding of Toxins and Identification of the Properties of Binders Experiment 4

Toxin at physiological levels of approx. 200 μg/L was mixed with a constant quantity (50 mg) of binder, agitated for 30 min, centrifuged and the toxin remaining in solution measured using a RIDASCREEN® FAST mycotoxin test kit (available from R-Biopharm GmbH, Darmstadt, Germany). The results are determined by reference to a standard binding curve for the toxin and binder.

Figure 1:
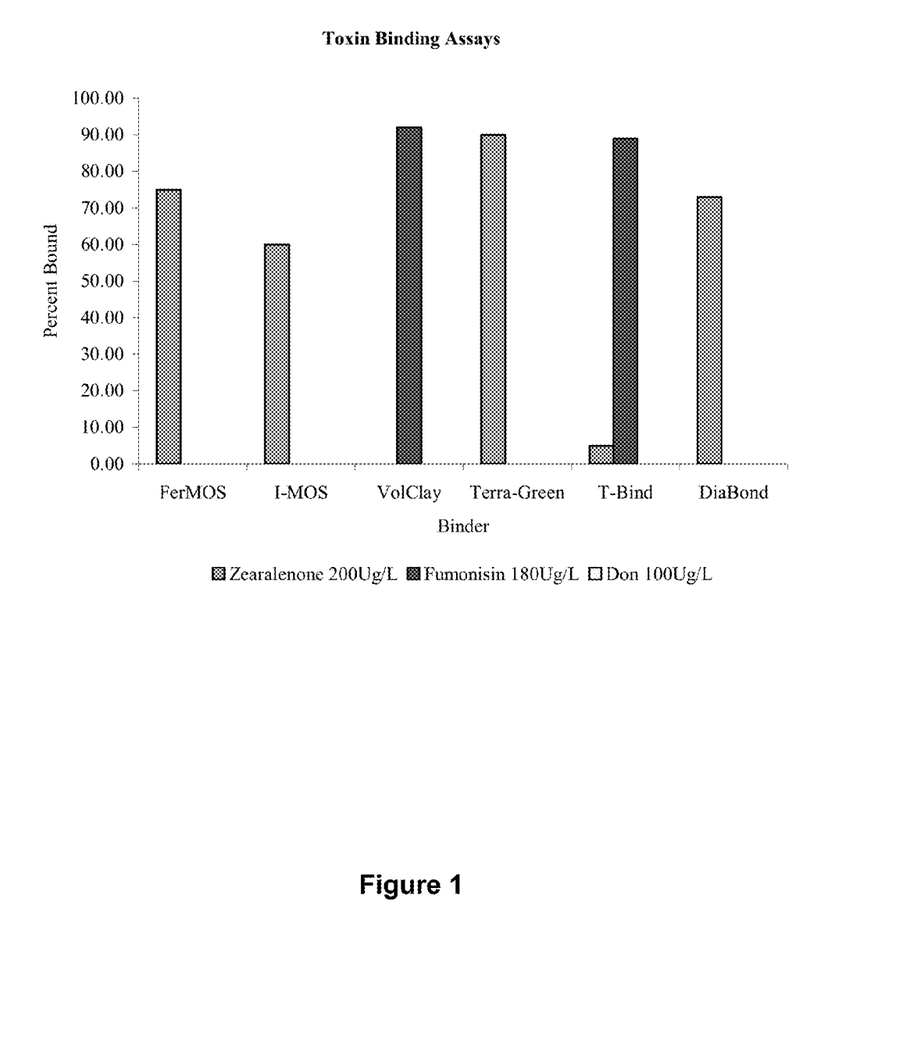
FIG. 1 is a graph indicating the binding percentage of various mycotoxins and mycotoxin-binding agents.

The results are shown in FIG. 1, which shows the binding percentage at a typical (physiological) rumen concentration. The binding abilities of various components are demonstrated at a physiological concentration of toxin. It can be seen from the variability in the results that a mixture of binders is preferable to a single entity. (Volclay=Na bentonite; Teragreen=Ca bentonite, FerMOS=polysaccharide binding complex).

Example C - Sequestration of Toxins and Subsequent Enzyme Degradation of the Toxin In the following experiments (5, 6, 7) active yeast cultures (Saccharomyces Cerevisiae NYCC R404) were charged with the appropriate toxin at 200μg/L and the disappearance from the supernatant followed by ELISA assays.

Figure 2:
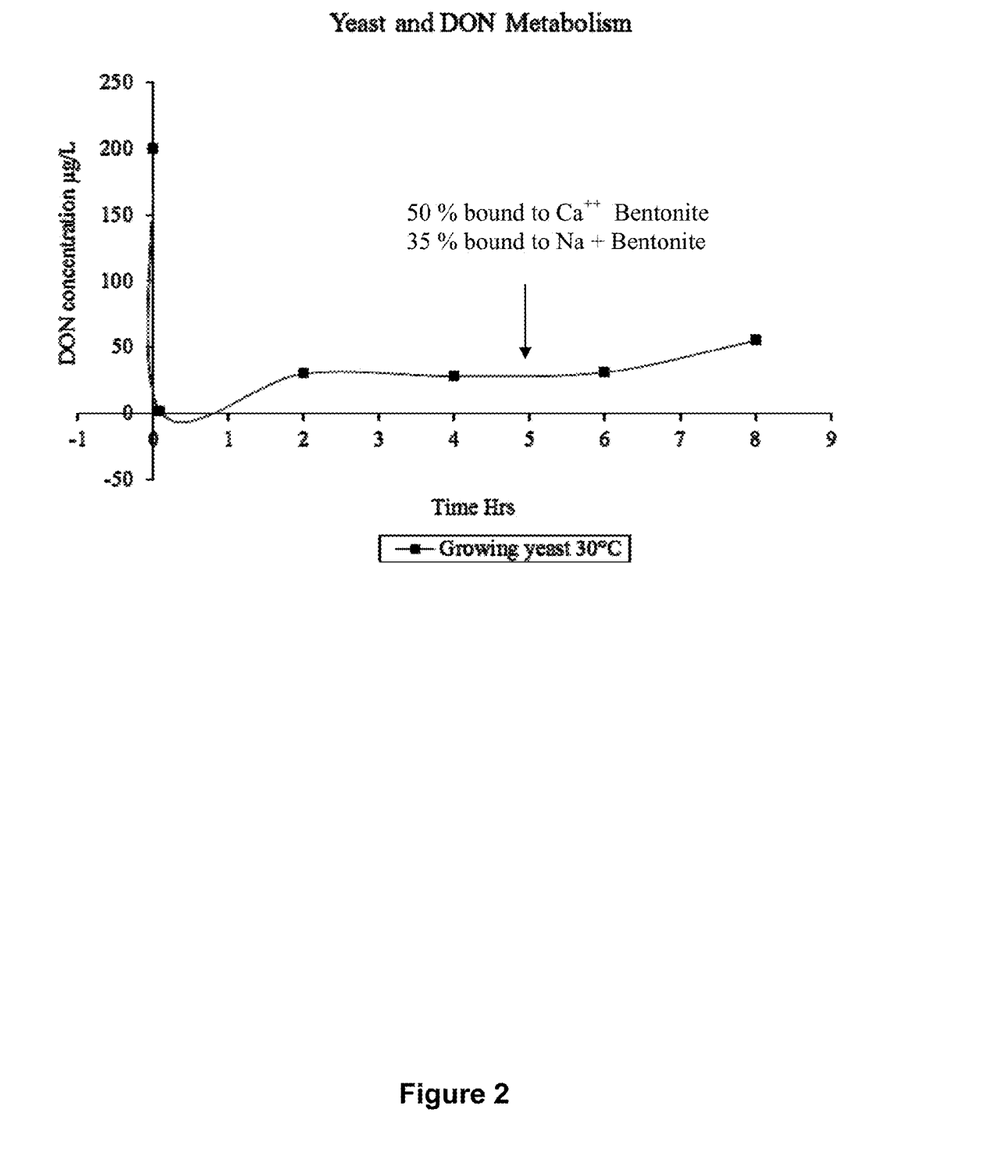
FIG. 2 illustrates the effect of Saccharomyces cerevisiae uptake of DON, which is then modified by the yeast, followed by release and binding of the modified toxin to bentonite.
Figure 3:
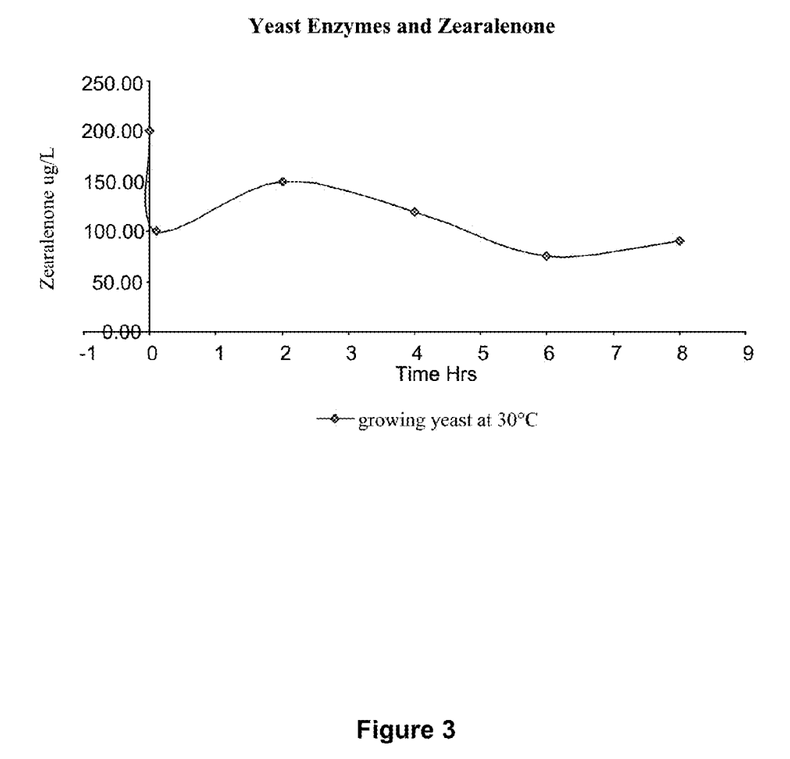
FIG. 3 illustrates the effect of Saccharomyces cerevisiae uptake of Zearalenone.
Figure 4:
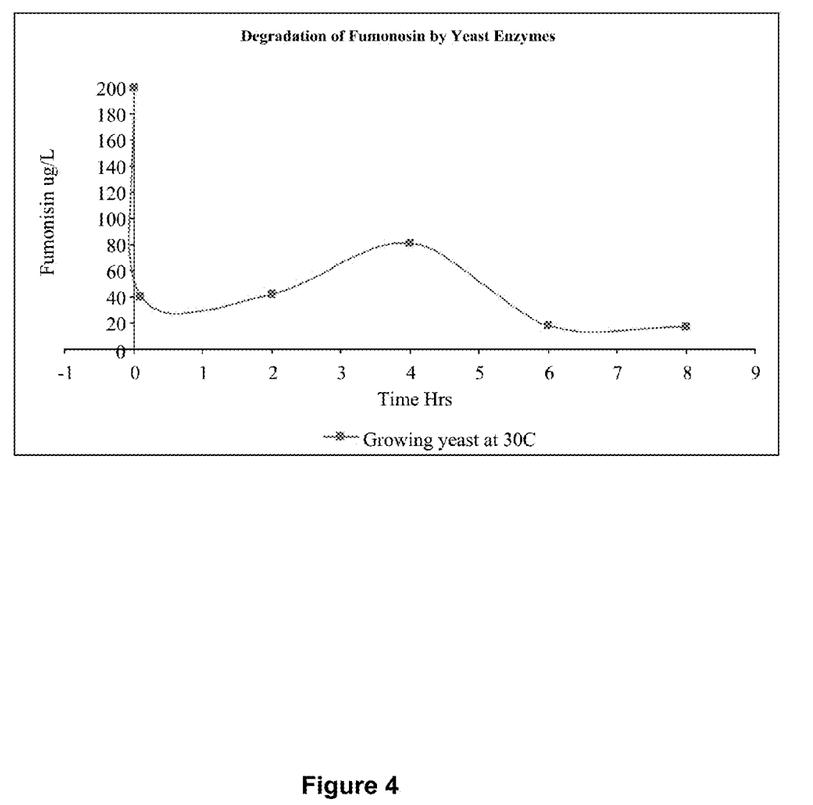
FIG. 4 illustrates the reduction of fumonisin using Saccharomyces cerevisiae.
Figure 5:
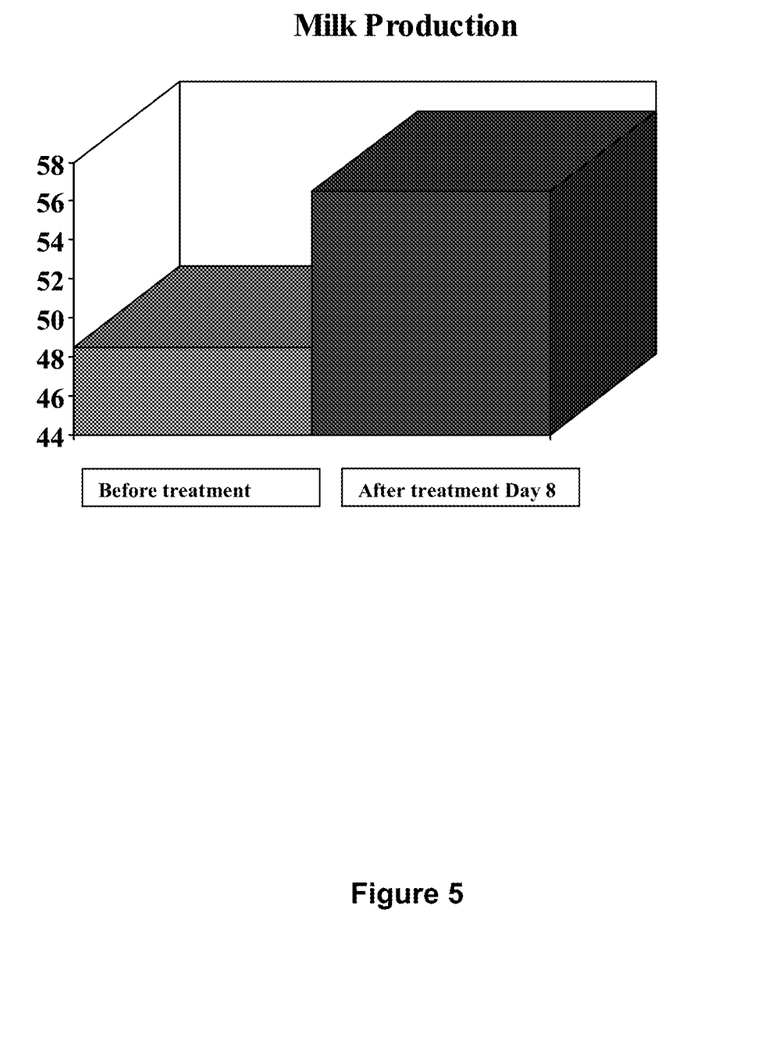
FIG. 5 shows the increase in milk production seen in a dairy herd, contaminated with Deoxynivalenol and Zearalenone, after application of a composition according to the invention.
Figure 6:
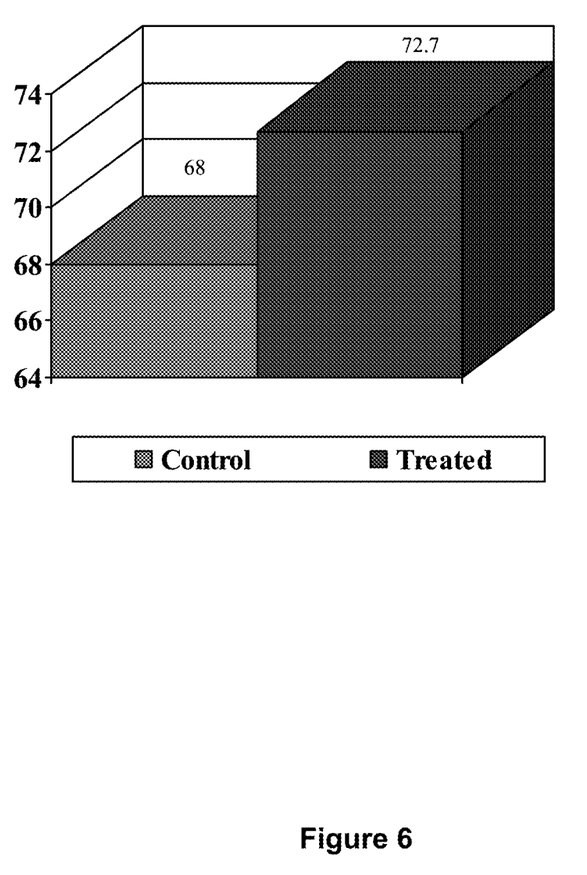
FIG. 6 shows the increase in milk production seen in a dairy herd, contaminated with Vomitoxin, after application of a composition according to the invention.

FIGS. 2, 3, and 4 illustrate the effects of the microorganism and its endogenous microbial enzymes on the mycotoxins DON, Zearalenone and Fumonisin. In each case, the yeast take up the toxin, rapidly reducing the toxicity of the culture. The toxin is then metabolised and released, in an altered form, where it is able to bind the binding agent, for subsequent degradation. These examples illustrate the synergy of the composition according to the invention.

Experiment 5: DON Uptake and Degradation by Yeast Enzymes

Yeast (Saccharomyces Cerevisiae NYCC R404) rapidly take up DON from solution, preventing uptake into the animal. The yeast metabolise the DON and release breakdown products (metabolites) which are able to bind to two different bentonite binders. Further degradation can then occur on the binders. See FIG. 2.

Experiment 6: Zearalenone Degradation by Yeast Enzymes

Rapid uptake by yeast (Saccharomyces Cerevisiae NYCC R404) is demonstrated with the toxin Zearalenone. The enzyme modification occurs in the cell and metabolite peak is then produced, as with DON, before it is subsequently degraded. See FIG. 3.

Experiment 7: Fumonisin Degradation by Yeast Enzymes

Yeast (*Saccharomyces Cerevisiae* NYCC R404) can remove fumonisin from the gastro-intestinal tract by sequestration, as shown in FIG. 4. Again, a peak of metabolites is produced early on before further degradation over time.

Example D - DON (Deoxynivalenol and Zearalenone) in a Dairy Herd

Treatment of a small herd receiving contaminated feed. Prior to treatment the 49 head herd exhibited rough hair coat, abortions, scours, erratic appetites, a lower and erratic milk production, feed in manure and stressed demeanour in the animals.

FIG. 5 shows that as the desired formulation (as defined in Table 1) was added, at a rate of 0.5 kilos /1000 kilos of feed for 2 days, and 0.25 kilos 1000 kilos of feed thereafter, milk production increased. Milk production is shown in lbs.

Example E - Deoxynivalenol (DON) in a Dairy Herd

Feed containing corn silage known to be contaminated with Vomitoxin (DON), and determined to be at 16.6 ppm, was fed to a 160 head dairy herd which was used in a one month experiment. Enzymes and binders (as part of the formulation defined in Table 1) were fed at 0.5 kilo per 1000 kilo of total mixed ration. Milk production is shown in FIG. 6, adjusted for 150 DIM.

Example F - Porcine Deoxynnivalenol

In a group of pigs where reproduction and growth performance was poor and the conception rate was less than 50%, the number born alive was at 5 pigs per litter. Grower finisher days were over 200 days and animals were very variable. A toxin challenge was identified. Feed analysis showed 4.1 and 4.8 ppm of DON. All breeding pigs were immediately placed on feed containing 2.5 kg/tonne of the formulation (as defined in Table 1).

After 21 days first service, conception was back to normal at over 90% and pigs born alive returned to Greater than 10 . Pig feed intake in grower finisher was back to normal. Subsequently, pig variation in grower finisher also returned to normal.

Boars also benefited. Exposed to DON, their semen volume and sperm concentration decreased by 50% within 7 days. On treatment they returned to normal also in approximately 7 days.

We claim:

1. A method of reducing the toxicity of a trichothecene mycotoxin in a foodstuff, comprising the step of contacting the foodstuff with a composition comprising an enzyme, a trichothecene mycotoxin-binding agent and a *Saccharomyces* yeast capable of taking up the trichothecene mycotoxin, wherein the enzyme is a combination of enzymes, and wherein the combination of enzymes comprises a cellulase, a hemicellulase, and a lipase.

2. The method according to claim 1, wherein the trichothecene mycotoxin is Deoxynivalenol.

3. The method according to claim 1, wherein the foodstuff is contacted with the composition prior to consumption by an animal.

4. The method according to claim 1, wherein the foodstuff is contacted with the composition simultaneous with consumption by an animal.

5. The method according to claim 1, wherein the enzyme potentiates the toxin binding to the trichothecene mycotoxin-binding agent.

6. The method of claim 1, wherein the trichothecene mycotoxin-binding agent has at least one charged surface.

7. The method of claim 1, wherein the trichothecene mycotoxin-binding agent is selected from among a zeolite, a montmorillonite, a bentonite clay, diatomaceous earth, activated charcoal, a fibrous plant material, a yeast cell wall extract, and a polysaccharide.

8. The method of claim 6, wherein the thrichothecene mycotoxin-binding agent comprises a bentonite.

9. The method of claim 1, wherein the *Saccharomyces* yeast is *Saccharomyces* cerevisiae.

10. The method of claim 1, wherein the foodstuff is of plant origin.

11. A method of reducing the toxicity of a trichothecene mycotoxin in a foodstuff, comprising the step of contacting the foodstuff with a composition comprising an enzyme, a trichothecene mycotoxin-binding agent and a *Saccharomyces* yeast capable of taking up the trichothecene mycotoxin, and wherein the foodstuff is of animal origin.

12. A method of reducing the toxicity of a trichothecene mycotoxin in a foodstuff comprising the step of contacting the foodstuff with a composition comprising an enzyme, a trichothecene mycotoxin-binding agent and a *Saccharomyces* yeast capable of taking up the trichothecene mycotoxin, and wherein the foodstuff comprises distiller's grain.

* * * * *